United States Patent
Abe et al.

(10) Patent No.: US 9,523,676 B2
(45) Date of Patent: Dec. 20, 2016

(54) LEUKOCYTE MEASUREMENT DEVICE AND REAGENT KIT

(75) Inventors: Toshiaki Abe, Shimotsuga-gun (JP); Atsufumi Wada, Shimotsuga-gun (JP); Mikito Ohyama, Shimotsuga-gun (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/237,090

(22) PCT Filed: Aug. 10, 2012

(86) PCT No.: PCT/JP2012/070514
§ 371 (c)(1),
(2), (4) Date: Feb. 4, 2014

(87) PCT Pub. No.: WO2013/027611
PCT Pub. Date: Feb. 28, 2013

(65) Prior Publication Data
US 2014/0212960 A1  Jul. 31, 2014

(30) Foreign Application Priority Data
Aug. 24, 2011 (JP) ................. 2011-182959

(51) Int. Cl.
G01N 33/50 (2006.01)
G01N 33/52 (2006.01)
G01N 33/558 (2006.01)

(52) U.S. Cl.
CPC ........ G01N 33/5091 (2013.01); G01N 33/523 (2013.01); G01N 33/558 (2013.01)

(58) Field of Classification Search
CPC . G01N 33/523; G01N 33/558; G01N 33/5091
See application file for complete search history.

(56) References Cited

U.S. PATENT DOCUMENTS 3,874,852 A   4/1975  Hamill
4,188,189 A * 2/1980  Allen .................... 436/505
(Continued)

FOREIGN PATENT DOCUMENTS

CN   1376779 A   10/2002
JP   51 6788     1/1976
(Continued)

OTHER PUBLICATIONS

International Preliminary Report on Patentability and Written Opinion issued Mar. 6, 2014, in International Application No. PCT/JP2012/070514.

(Continued)

*Primary Examiner* — Jill Warden
*Assistant Examiner* — Matthew Krcha
(74) *Attorney, Agent, or Firm* — Oblon, McClelland, Maier & Neustadt, L.L.P.

(57) ABSTRACT

A leukocyte measurement device is provided with a spread inspection window at a position separated from an opening part along a spreading direction of a blood-derived sample in a carrier, for making the carrier visible from outside. When the blood-derived sample is dropped from the opening part, leukocytes contained in the blood-derived sample are captured by the carrier in the vicinity of a dropping position, while erythrocytes and/or hemoglobin and the like spread through the carrier from the dropping position into a predetermined direction. Therefore, in the leukocyte measurement device, seeing through the spread inspection window the color of the erythrocytes and/or hemoglobin spread from the dropping position can determine whether it has already been used or not, whereby a simple structure can prevent measurers from erroneously reusing it.

5 Claims, 10 Drawing Sheets

(56) References Cited

U.S. PATENT DOCUMENTS

| | | | |
|---|---|---|---|
| 5,190,657 A | 3/1993 | Heagle et al. | |
| 5,290,449 A | 3/1994 | Heagle et al. | |
| 5,416,026 A * | 5/1995 | Davis | G01N 33/725 |
| | | | 436/169 |
| 5,454,946 A | 10/1995 | Heagle et al. | |
| 6,004,821 A * | 12/1999 | Levine et al. | 436/169 |
| 6,036,659 A * | 3/2000 | Ray et al. | 600/573 |
| 6,171,870 B1 | 1/2001 | Freitag | |
| 2003/0113925 A1 | 6/2003 | Gordon et al. | |
| 2003/0215951 A1 | 11/2003 | Law et al. | |
| 2005/0106552 A1* | 5/2005 | Ikeda | G01N 33/491 |
| | | | 435/2 |
| 2005/0130120 A1 | 6/2005 | Lambotte et al. | |
| 2006/0024757 A1* | 2/2006 | Hussa et al. | 435/7.2 |
| 2006/0088941 A1 | 4/2006 | Law et al. | |
| 2006/0246598 A1 | 11/2006 | Dai et al. | |
| 2008/0085525 A1* | 4/2008 | Van Herwijnen | G01N 33/558 |
| | | | 435/7.25 |
| 2008/0269706 A1 | 10/2008 | Long et al. | |
| 2009/0029453 A1 | 1/2009 | Lambotte et al. | |
| 2010/0015634 A1* | 1/2010 | VanDine et al. | 435/7.1 |
| 2010/0159444 A1 | 6/2010 | Lambotte et al. | |

FOREIGN PATENT DOCUMENTS

| | | |
|---|---|---|
| JP | 7 500003 | 1/1995 |
| JP | 7 31677 | 2/1995 |
| JP | 2005 526513 | 9/2005 |
| JP | 2007 506115 | 3/2007 |
| JP | 2008-275627 A | 11/2008 |
| JP | 2010 181346 | 8/2010 |
| JP | 2010 526564 | 8/2010 |
| WO | WO 02/01229 A1 | 1/2002 |
| WO | 2005/014553 A1 | 1/2005 |
| WO | WO2010/111536 A1 | 9/2010 |

OTHER PUBLICATIONS

International Search Report Issued Sep. 11, 2012 in PCT/JP12/070514 Filed Aug. 10, 2012.

Supplementary European Search Report mailed on Mar. 3, 2015 in EP Application No. 12 82 5829, 7 pp.

Notice of Allowance issued Aug. 2, 2016 in Japanese Patent Application No. 2013-529968.

* cited by examiner

|  | Case 1 | Case 2 | Case 3 | Case 4 |
|---|---|---|---|---|
| Opening part | coloration*1 | coloration*2 | no coloration | coloring*3 |
| Spread inspection window | coloring | no coloring | coloring | no coloring |
| Measurement results | appropriate | inappropriate | appropriate | inappropriate |
| Remeasurement | unnecessary | necessary | unnecessary | necessary |

*1 : There is reagent coloration by leukocytes.
*2 : There are reagent coloration by leukocytes and coloring by erythrocytes and/or hemoglobin.
*3 : There is no reagent coloration by leukocytes but coloring by erythrocytes and/or hemoglobin.

LEUKOCYTE MEASUREMENT DEVICE AND REAGENT KIT

TECHNICAL FIELD

The present invention relates to a leukocyte measurement device and a reagent kit.

BACKGROUND ART

Leukocytes are one of components contained in the blood and act to remove foreign materials having intruded into the body from the outside. Either when infected with bacteria or viruses, a human body develops a fever. The number of leukocytes increases in the case of bacteria infection, whereas the number of lymphocytes increases but the number of leukocytes is held normal or decreases in the case of virus infection. Therefore, measuring leukocytes can distinguish between the bacterial infection and the virus infection.

Automatic blood cell counters utilizing electric resistivity methods have conventionally been used for measuring leukocytes (see, for example, Patent Literature 1). However, since the automatic blood cell counters are special instruments with a large size, leukocyte measurement devices which enable POC (Point of Care) tests at the time of examining outpatients in small- and medium-sized hospitals and at bedside have been desired.

An example of such leukocyte measurement devices is one using a carrier such as a porous membrane. For example, Patent Literature 2 discloses a leukocyte measurement device which measures the peroxidase activity due to myeloperoxidase in leukocytes (granulocytes in particular). This leukocyte measurement device lyses or disrupts leukocytes, so as to release myeloperoxidase, and then detects how a hydrogen peroxide decomposition reaction is promoted by the myeloperoxidase according to a change in the color of an oxidation-sensitive chromogenic donor dye on a porous membrane.

For example, Patent Literature 3 discloses a leukocyte measurement device using the esterase activity as an indicator. This leukocyte measurement device detects the hydrolysis activity due to esterase according to coloration of a chromogenic substrate such as 3-acetyl indoxyl on a porous membrane. When using this leukocyte measurement device, the blood of a subject as whole blood is dropped onto the device, so as to capture leukocytes, other blood components such as erythrocytes are removed with a wash solution as being caused to flow down therethrough, and then the esterase activity is measured.

CITATION LIST

Patent Literature

Patent Literature 1: Japanese Patent Application Laid-Open No. S51-006788
Patent Literature 2: Japanese Translated International Application Laid-Open No. H07-500003
Patent Literature 3: Japanese Translated International Application Laid-Open No. 2005-526513

SUMMARY OF INVENTION

Technical Problem

However, in order to perform accurate leukocyte measurement, the above-mentioned leukocyte measurement device of Patent Literature 2 necessitates cumbersome preprocessing for completely separating leukocytes from the other blood components before the measurement because the other blood components such as erythrocytes and plasma contain peroxidase and also because hemoglobin in erythrocytes has a peroxidase-like activity.

On the other hand, the leukocyte measurement device of Patent Literature 3 requires no cumbersome preprocessing but is problematic in that there is no means for easily determining whether or not the device has already been used when the number of leukocytes in the blood of a subject is small after dropping the blood onto the device or when the measurement is not performed appropriately because of faults in the carrier and the like. Hence, there is a fear of measurers erroneously reusing the used leukocyte measurement device.

For solving the problems mentioned above, it is an object of the present invention to provide a leukocyte measurement device and a reagent kit which, in a simple structure, can prevent them from being erroneously reused by measurers.

Solution to Problem

For solving the above-mentioned problems, the leukocyte measurement device in accordance with the present invention comprises a housing provided with an opening part for dropping a blood-derived sample and a carrier, contained in the housing, for capturing leukocytes in components contained in the blood-derived sample dropped from the opening part near a dropping position thereof and spreading the other components into a predetermined direction, wherein the housing is provided with a spread inspection window, located at a position separated from the opening part in the spreading direction of the other components, for making the carrier visible from outside.

In the leukocyte measurement device, a spread inspection window for making the carrier visible from outside is disposed at a position separated from the opening part along the spreading direction of the blood-derived sample caused by a lateral flow in the carrier. When the blood-derived sample is dropped from the opening part, leukocytes contained in the blood-derived sample are captured by the carrier in the vicinity of the dropping position, while erythrocytes and/or hemoglobin and the like spread through the carrier from the dropping position into a predetermined direction. Therefore, in the leukocyte measurement device, seeing through the spread inspection window the color of the erythrocytes and/or hemoglobin spread from the dropping position can determine whether it has already been used or not, whereby a simple structure can prevent measurers from erroneously reusing it.

Preferably, at least one such spread inspection window is provided along the spreading direction. When at least one spread inspection window is provided, the state of spread of erythrocytes and/or hemoglobin can be seen more securely.

Preferably, the sample dropping position of the carrier is impregnated with a part or whole of a reagent for a color reaction by leukocytes. Seeing the color at the opening part and the color at the spread inspection window can determine whether or not the leukocyte measurement device has already been used and measure leukocytes (qualitatively or quantitatively) at the same time.

The reagent kit in accordance with the present invention comprises the above-mentioned leukocyte measurement device and at least one of a reagent for a color reaction by leukocytes, a wash solution, and a diluent.

The reagent kit is provided with the spread inspection window for making the carrier visible from outside at a position separated from the opening part along the spreading direction of the blood-derived sample caused by a lateral flow in the carrier. When the blood-derived sample is dropped from the opening part, leukocytes contained in the blood-derived sample are captured by the carrier in the vicinity of the dropping position, while erythrocytes and/or hemoglobin and the like spread through the carrier from the dropping position into a predetermined direction. Therefore, seeing through the spread inspection window the color of the erythrocytes and/or hemoglobin spread from the dropping position can determine whether it has already been used or not, whereby a simple structure can prevent measurers from erroneously reusing it.

Advantageous Effects of Invention

In a simple structure, the leukocyte measurement device and reagent kit in accordance with the present invention can prevent them from being erroneously reused by measurers. They also make it possible to determine whether or not measurement is performed appropriately without necessitating a control coloring reagent.

DESCRIPTION OF EMBODIMENTS

In the following, preferred embodiments of the leukocyte measurement device and reagent kit in accordance with the present invention will be explained in detail with reference to the drawings. In the following explanation, the same constituents will be referred to with the same signs while omitting their overlapping descriptions.

Figure 1:
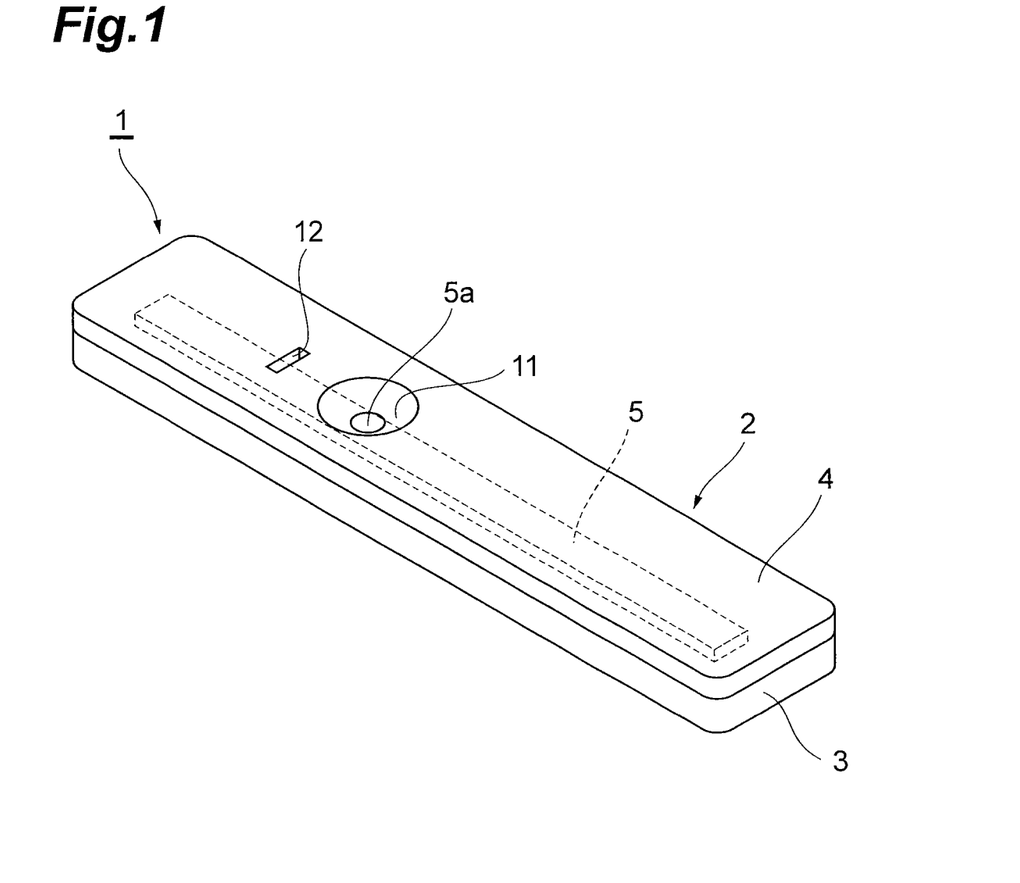
FIG. 1 is a perspective view illustrating an embodiment of the leukocyte measurement device in accordance with the present invention.
Figure 2:
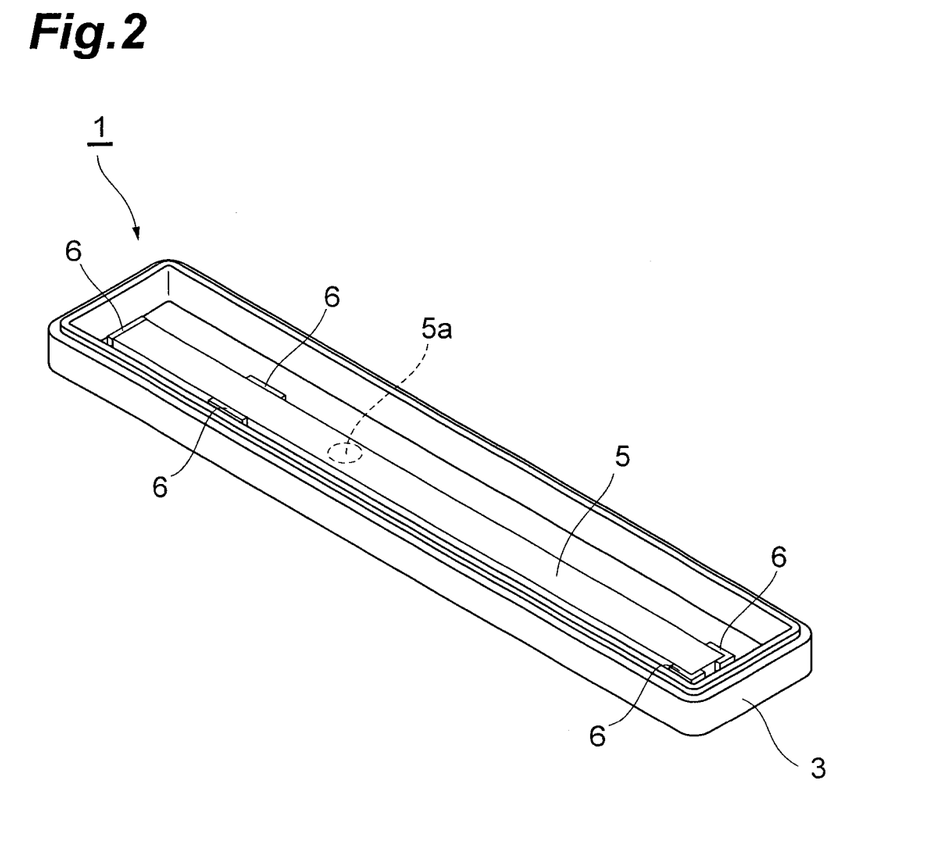
FIG. 2 is a perspective view illustrating the leukocyte measurement device of FIG. 1 without its lid part.

FIG. 1 is a perspective view illustrating an embodiment of the leukocyte measurement device in accordance with the present invention. FIG. 2 is a perspective view illustrating the leukocyte measurement device of FIG. 1 without its lid part. As FIGS. 1 and 2 illustrate, a leukocyte measurement device 1 is constituted by a flat rectangular parallelepiped housing 2, which comprises a main part 3 and a lid part 4, and a strip-like carrier 5 arranged within the housing 2. The leukocyte measurement device 1 is a device for measuring leukocytes contained in a blood-derived sample S (see FIG. 3) and, when the blood-derived sample S is dropped on the carrier 5 in the housing 2, captures the leukocytes at a dropping position 5a, while spreading the other blood components such as erythrocytes through the carrier 5, so as to separate them.

The blood-derived sample S to be measured is a sample containing at least erythrocytes and leukocytes. That is, the blood-derived sample S may be any of whole blood, one in which whole blood is diluted with a diluent, and one selectively containing erythrocytes and leukocytes. The diluent may be any of isotonic solutions, examples of which include normal saline and phosphate-buffered saline. It is preferred for the volume of collected blood to be suppressed from the viewpoint of lessening the burden on subjects, while it is preferred for the blood-derived sample S to have a sufficient amount from the viewpoint of securing accuracy in measurement.

In view of the above, the amount of the blood-derived sample S is preferably on the order of 1 µl to 100 µl, more preferably on the order of 3 µl to 50 µl, further preferably on the order of 5 µl to 10 µl in the case of whole blood. In the case of diluted blood, the amount is preferably on the order of 100 µl to 350 µl in view of the migration length of erythrocytes and/or hemoglobin in the carrier 5, which will be explained later. In the case of the sample selectively containing erythrocytes and leukocytes, the amount is preferably on the order of 3 µl to 350 µl, more preferably on the order of 5 µl to 100 µl.

After dropping the blood-derived sample S, a reaction reagent solution or a wash solution may further be dropped, so as to promote the separation between leukocytes and erythrocytes and the spread of erythrocytes. This method is effective when the amount of the blood-derived sample S is minute (in particular when only a minute amount of the sample is available for using whole blood). While the wash solution is not limited in particular as long as it does not affect the reaction for leukocyte measurement, normal saline, phosphate-buffered saline, distilled water, and purified water, for example, are used preferably from the viewpoints of cost and influence on leukocyte measurement. Solutions containing surfactants such as saponin, Triton (registered trademark) X-100, and sodium dodecyl sulfate can also be used.

The reaction reagent solution is a solution for a reaction by leukocytes, i.e., a reagent for a color reaction based on enzymes or proteins within leukocytes, surface antigens thereof, or the like. While the reaction reagent solution may be used as appropriate according to the leukocyte measurement method, TMB Solution (manufactured by Wako Pure Chemical Industries, Ltd.) containing hydrogen peroxide and 3,3',5,5'-tetramethylbenzidine (TMB) can be used for performing myeloperoxidase POD activity measurement illustrated in Example 4 which will be explained later, for instance. When performing leukocyte esterase activity measurement illustrated in Example 5 which will be explained later, for instance, a 0.1 M boric acid buffer having a pH of 8.6 can be used. However, 3-(N-tosyl-L-alanyloxy)indole, which is an esterase substrate, is dried beforehand in the carrier impregnated therewith. When performing enzyme immunoassay illustrated in Example 6 which will be explained later, for instance, a solution diluting an enzyme-labeled antibody (ALP-labeled antineutrophil antibody) with a 10 mM phosphate-buffered solution at a pH of 7.2 containing 150 mM NaCl, and BCIP/NBT Phosphatase Substrate (manufactured by Kirkegaard & Perry Laboratories, Inc.) can be used.

When anisotonic wash solutions such as distilled water, purified water, and surfactant-containing solutions or reaction reagent solutions are dropped, erythrocytes and leukocytes lyse, while leukocytes release enzymes and the like from therewithin as they lyse, thereby achieving the effect of promoting the leukocyte measurement reaction. As erythrocytes lyse, hemoglobin flows out, thereby spreading through the carrier 5 as with erythrocytes. After dropping the sample, wash solution, and reaction agent, a reaction termination solution may further be dropped so as to stop the reaction from advancing. In this case, the leukocyte measurement can easily be performed without bothering about the time required for determining results of the measurement.

Constituents of the leukocyte measurement device 1 will now be explained in detail. The housing 2 is an opaque or semitransparent member for covering the carrier 5 mainly in order to prevent measurers from being infected and measurement environments from being contaminated. The main part 3 of the housing 2 is a bottomed container which opens on one side, while the inner face of the bottom portion of the main part 3 is provided with a plurality of guides 6 for positioning the carrier 5. The lid part 4 is detachably attachable to the main part 3. Attaching the lid part 4 to the main part 3 while the carrier 5 is set to the main part 3 with the guides 6 achieves a state ready for leukocyte measurement. The main part 3 and lid part 4 may be joined together through a hinge.

While materials for the housing 2 are not restricted in particular as long as they do not obstruct the measurement, their examples include thermoplastic resins such as ABS (acrylonitrile-butadiene-styrene) resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate and thermosetting resins such as phenol resin, epoxy resin, silicone resin, and unsaturated polyester.

As FIG. 1 illustrates, the lid part 4 of the housing 2 is formed with a circular opening part 11 for dropping the blood-derived sample S and a rectangular spread inspection window 12 for seeing how the blood-derived sample S spreads through the carrier 5. The opening part 11 is tapered such as to reduce its diameter gradually from the outer wall side to inner wall side of the lid part 4, thus ensuring it easy for the blood-derived sample S to flow toward the carrier 5.

The spread inspection window 12 is separated from the opening part 11 by a predetermined distance longitudinally of the carrier 5 when seen from the opening part 11 and exposes the carrier 5 from within the housing 2 at this position. The distance between the opening part 11 and the spread inspection window 12 can be changed as appropriate according to the amount of the blood-derived sample S dropped, the pore size, thickness, and width of a fiber filter (which will be explained later) constituting the carrier 5, and the like.

Preferably, the distance is made longer and shorter as the amount of the blood-derived sample S dropped is greater and smaller, respectively. Preferably, the distance is made longer and shorter as the pore size of the fiber filter is greater and smaller, respectively. Preferably, the distance is made longer and shorter as the thickness of the fiber filter is smaller and greater, respectively. Preferably, the distance is made longer and shorter as the width of the carrier 5 is smaller and greater, respectively. In view of the usability, cost, and the like of the leukocyte measurement device 1, the distance is preferably at least 5 mm but preferably 100 mm or less, more preferably 50 mm or less.

The spread inspection window 12 may be shaped into any of circles, ellipses, polygons, stars, and the like as well as rectangles as mentioned above. Preferably, the opening part 11 and spread inspection window 12 are shaped into forms different from each other, or the spread inspection window 12 is made smaller than the opening part 11. This can prevent measurers from erroneously dropping the blood-derived sample S onto the spread inspection window 12. The spread inspection window 12 may be an opening or an opening with a transparent film or the like attached thereto as long as it can make the carrier 5 visible from outside. The spread inspection window 12 may be configured such as to make the housing 2 transparent at its position. The spread inspection window 12 may have a form elongated longitudinally of the housing 2. In addition to the spread inspection window 12, the housing 2 may be provided with a vent for promoting the spread of the blood-derived sample S, and absorbent pads may be arranged within the housing 2 for the same purpose.

Preferably, a color which does not hinder the color of the carrier 5 seen from the opening part 11 and spread inspection window 12 from being identified is selected for the housing 2. For example, the color of erythrocytes and/or hemoglobin is red immediately after being dropped onto the carrier 5 but changes to dark brown with time. Therefore, it is preferred for the housing 2 to avoid colors ranging from red to dark brown.

In preferred values of the color of the housing 2 represented according to the xy chromaticity diagram (CIE 1931) in the Yxy color space of the International Commission on Illumination (CIE), the value of x is preferably 0.6 or less, while the value of Y is not restricted. When the value of x is 0.5 or greater, the value of y is preferably 0.3 or greater, more preferably 0.4 or greater. When the value of x is 0.4 or greater, y is preferably 0.2 or greater, more preferably 0.25 or greater. When the value of x is 0.32 or greater, y is preferably 0.15 or greater, more preferably 0.2 or greater. When the value of x is less than 0.32, the value of y is not limited in particular. In the Yxy color space, the value of Y is the reflectance corresponding to the brightness, while x and y indicate the chromaticity.

The carrier 5 is a member for capturing and separating leukocytes contained in the blood-derived sample S. The carrier 5, whose size can be set as appropriate in view of the amount of the blood-derived sample, the cost of the carrier 5, and the like, is shaped into a strip having a width on the order of 3 mm to 7 mm, a length on the order of 20 mm to 150 mm, and a thickness on the order of 0.3 mm to 1.2 mm when the housing 2 has a flat, substantially rectangular parallelepiped form as in the leukocyte measurement device 1. For spreading erythrocytes, hemoglobin, and other liquid components by a lateral flow, the thickness of the carrier 5 is preferably 0.3 mm to 1.2 mm, more preferably 0.7 mm to 1.0 mm. In this case, the housing 2 may have an area defined by a width on the order of 3 mm to 20 mm and a length on the order of 20 mm to 160 mm, for example. The thickness of the housing 2 is preferably 0.5 mm to 15 mm, more preferably 1 mm to 8 mm. The size and thickness of the housing 2 can be set as appropriate in view of the structure, usability, and cost of the leukocyte measurement device in accordance with the present invention and the area, thickness, and the like of the carrier 5. The carrier 5 may be shaped into any of rectangles, circles, and the like as well as strips as mentioned above and preferably has each side on the order of 20 mm to 50 mm when rectangular and a diameter on the order of 20 mm to 50 mm when circular. The housing 2 preferably has each side on the order of 20 mm to 60 mm when the carrier 5 is rectangular and a diameter on the order of 20 mm to 60 mm when the carrier 5 is circular.

While materials for the carrier 5 are not restricted in particular as long as they can uniformly capture leukocytes, their examples include fiber filters using synthetic fibers such as polyurethane, polyvinylidene fluoride, polysulfone, polyethylene, polypropylene, cellulose acetate, polyester, polyamide, and polyacrylonitrile, inorganic fibers such as glass fibers, and natural fibers such as cellulose, cotton, silk, and wool.

The pore size of the fiber filter is on the order of 3 μm to 10 μm, for example, so as to be suitable for capturing and separating leukocytes. For improving the leukocyte capture efficiency, a fiber filter having a positive surface charge or one coated with a material selectively attachable to leukocytes such as a copolymer of hydroxyethyl methacrylate and diethylaminoethyl methacrylate may be used.

The carrier 5 is arranged within the housing 2 while being positioned by the guides 6 of the main part 3 so as to overlap the opening part 11 and spread inspection window 12 in a planar view as illustrated in FIG. 2. In the carrier 5, a part overlapping the opening part 11 becomes a dropping position 5a where the blood-derived sample S is dropped. The dropping position 5a may be impregnated beforehand with a part or whole of a reagent for a color reaction by leukocytes.

The reagent is selected as appropriate according to the leukocyte measurement method. The leukocyte measurement method is not limited in particular as long as it is based on enzymes or proteins within leukocytes or surface antigens thereof. While examples of the leukocyte measurement method include methods by which results of measurement of coloration based on activities of leukocyte-derived enzymes such as leukocyte esterase, elastase, and myeloperoxidase and results of measurement of elastase, myeloperoxidase, lactoferrin, neutrophils, CD4, and the like by immunoassays are converted into the number of leukocytes, the leukocyte measurement device 1 can also perform methods for measuring enzyme activities within leukocytes and the like in addition to the measurement of the number of leukocytes. Each measurement may be either qualitative or quantitative. The coloration measurement is performed by a predetermined optical device or visual observation.

Figure 3:
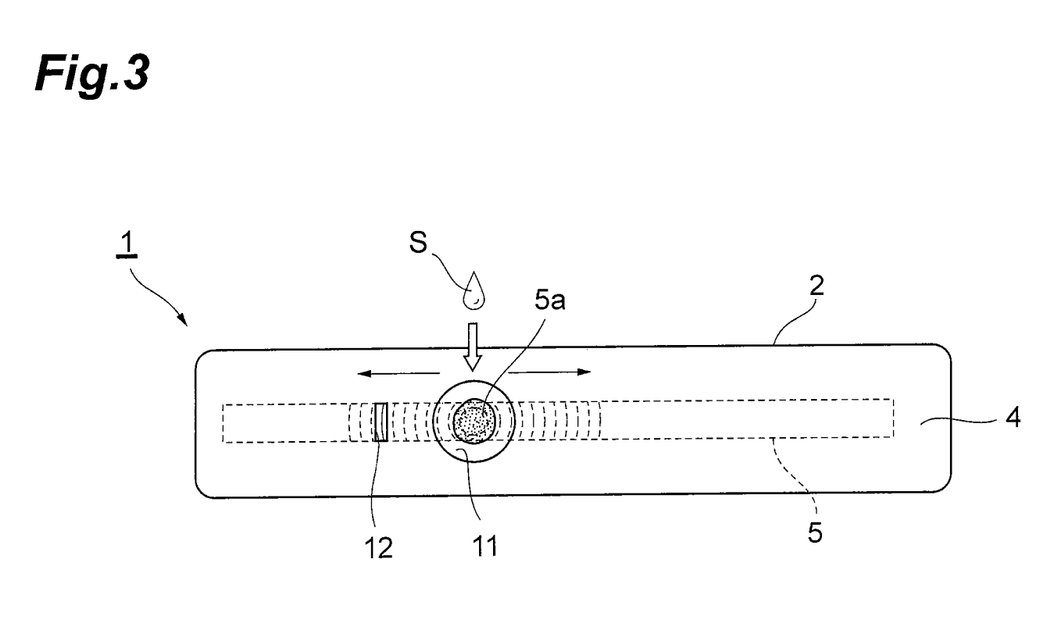
FIG. 3 is a plan view illustrating how a blood-derived sample spreads through a carrier.

When the blood-derived sample S is dropped from the opening part 11 onto the carrier 5 in thus constructed leukocyte measurement device 1 as illustrated in FIG. 3, only leukocytes in components contained in the blood-derived sample S are captured near its dropping position 5a. On the other hand, the other components such as erythrocytes and hemoglobin pass through the fiber filter together with liquid components by capillary actions and mainly spread longitudinally of the carrier 5. At the dropping position 5a, coloration is caused by a reaction between the reagent and enzymes or proteins within leukocytes or surface antigens thereof, and qualitative measurement of leukocytes (determination of whether leukocytes are normal or abnormal), quantitative measurement of the number of leukocytes, qualitative or quantitative measurement of enzyme activities within leukocytes, and the like are performed according to the state of coloration.

On the other hand, the leukocyte measurement device 1 is provided with the spread inspection window 12 for exposing the carrier 5 at a position separated from the opening part 11 along the spreading direction of the blood-derived sample S in the carrier 5. Therefore, seeing through the spread inspection window 12 the color of erythrocytes and/or hemoglobin spread from the dropping position 5a can determine whether the leukocyte measurement device 1 has already been used or not, whereby a simple structure can prevent measurers from erroneously reusing it. The erythrocytes and/or hemoglobin spread to the position of the spread inspection window 12 stays there after the completion of measurement. Hence, whether the leukocyte measurement device 1 has already been used or not can be determined even after a lapse of time.

The leukocyte measurement device 1 can be constructed as a reagent kit bundled with at least one of the reaction reagent, wash solution, and diluent. A reagent kit can also be constructed such that the reaction reagent is contained as a liquid reagent in a space within the leukocyte measurement device 1. The reagent kit may further contain a reaction termination solution, a color tone table for determining the coloration by leukocytes, a puncture device for collecting the blood, and the like.

Figure 4:
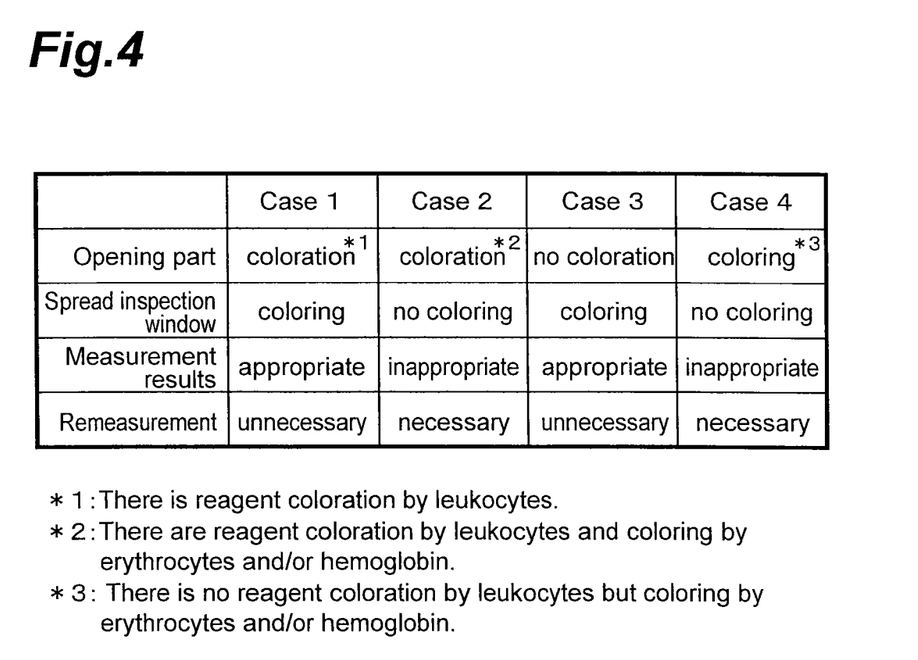
FIG. 4 is a chart illustrating relationships between the reagent coloration by leukocytes and coloring by erythrocytes and/or hemoglobin in the opening part and spread inspection window and whether or not measurement results of leukocytes are appropriate.

Relationships between the reagent coloration by leukocytes and coloring by erythrocytes and/or hemoglobin in the opening part 11 and spread inspection window 12 and whether or not measurement results of leukocytes are appropriate when using the leukocyte measurement device 1 are as illustrated in FIG. 4. As this chart illustrates, when the reagent coloration by leukocytes and the coloring by erythrocytes and/or hemoglobin are respectively seen in the opening part 11 and spread inspection window 12 (case 1), the measurement results are appropriate, whereby no remeasurement is necessary. When the reagent coloration by leukocytes and the coloring by erythrocytes and/or hemoglobin are seen in the opening part 11 while no coloring by erythrocytes and/or hemoglobin is seen in the spread inspection window 12 (case 2), the measurement results are inappropriate, whereby remeasurement is necessary. When no reagent coloration by leukocytes is seen in the opening part 11 while the coloring by erythrocytes and/or hemoglobin is seen in the spread inspection window 12 (case 3), the measurement results are appropriate, whereby no remeasurement is necessary. When no reagent coloration by leukocytes is seen in the opening part 11 while no coloring by erythrocytes and/or hemoglobin is seen in the spread inspection window 12 (case 4), the measurement results are inappropriate, whereby remeasurement is necessary. As in the foregoing, seeing whether or not there is coloring by erythrocytes and/or hemoglobin in the spread inspection window 12 after a predetermined time from the dropping of the blood-derived sample S from the opening part 11 can determine whether the measurement is performed appropriately or not in the leukocyte measurement device 1.

When the coloring by erythrocytes and/or hemoglobin is seen in the spread inspection window 12, determining whether or not leukocytes are within a normal range, at a high level, and so forth, conversion to the number of leukocytes, and the like are performed by comparing the degree of reagent coloration by leukocytes in the opening part 11 with a reference set in a predetermined measurement method. When no coloring by erythrocytes and/or hemoglobin is seen in the spread inspection window 12, there is a high possibility of leukocytes being separated unfavorably so that blood components other than leukocytes remain at the dropping position 5a, thereby affecting the leukocyte measurement reaction. The components other than leukocytes may either suppress or promote coloration. Therefore, regardless of whether or not there is reagent coloration by leukocytes in the opening part 11, it is necessary to determine that the measurement results are inappropriate and perform remeasurement.

Figure 5:
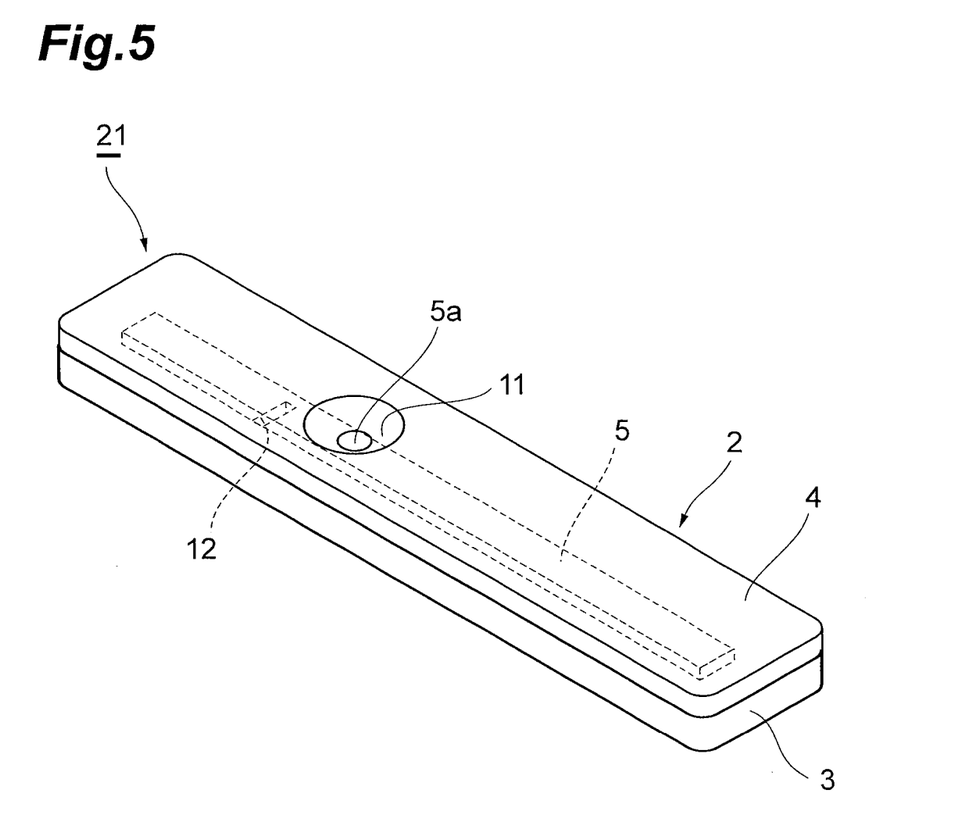
FIG. 5 is a perspective view illustrating the leukocyte measurement device in accordance with a modified example of the present invention.
Figure 6:
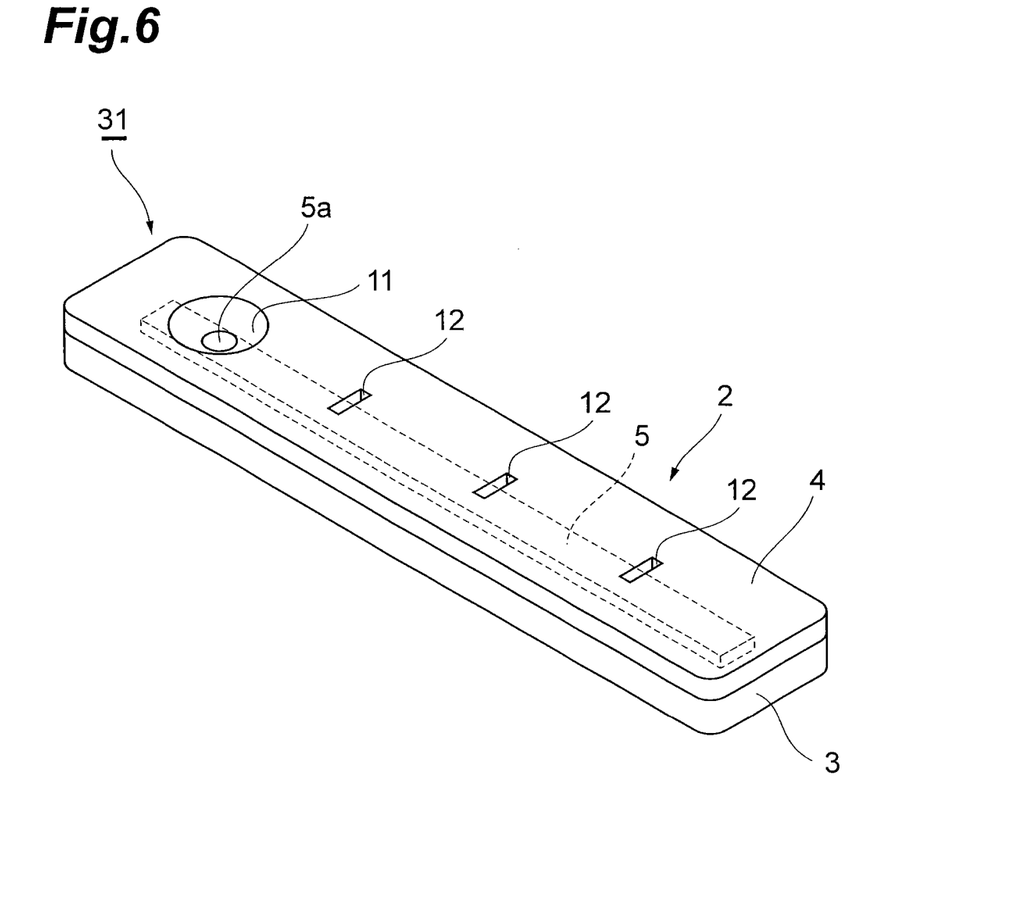
FIG. 6 is a perspective view illustrating the leukocyte measurement device in accordance with another modified example of the present invention.

The present invention is not limited to the above-mentioned embodiment. For example, while the lid part 4 of the housing 2 is provided with the opening part 11 and spread inspection window 12 in the above-mentioned embodiment, the lid part 4 of the housing 2 and the main part 3 may be provided with the opening part 11 and spread inspection window 12, respectively, as in a leukocyte measurement device 21 illustrated in FIG. 5. For example, as in a leukocyte measurement device 31 illustrated in FIG. 6, the opening part 11 may be disposed on one longitudinal end side of the lid 4, and a plurality of spread inspection windows 12 may be formed in a row longitudinally of the carrier 5 from the opening part 11 to the other end side of the lid part 4. In this case, the state of spread of erythrocytes and/or hemoglobin can be seen in more detail.

Figure 7:
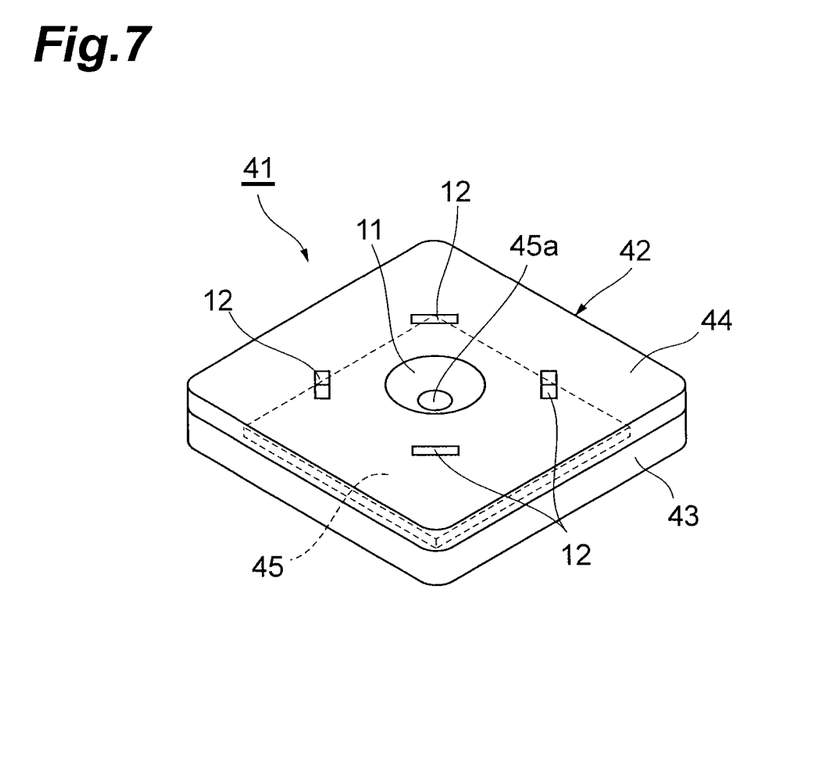
FIG. 7 is a perspective view illustrating the leukocyte measurement device in accordance with still another modified example of the present invention.

While the above-mentioned embodiment uses the strip-like carrier 5, a square carrier 45 may be used as in a leukocyte measurement device 41 illustrated in FIG. 7, for example. In this case, a housing 42 may have a form which is seen as a square in a planar view in conformity to the shape of the carrier 45. In the example illustrated in FIG. 7, the opening part 11 is disposed at the center on the upper face of a lid part 44 of the housing 42, while four spread inspection windows 12 are formed about the opening part 11 so as to correspond to four corners of the carrier 45, respectively. When the blood-derived sample S is dropped onto the carrier 45 in this example, erythrocytes and/or hemoglobin spreads radially from a dropping position 45a. Therefore, forming the spread inspection windows 12 at the positions mentioned above makes it easy to see the state of spread of erythrocytes and/or hemoglobin.

Figure 8:
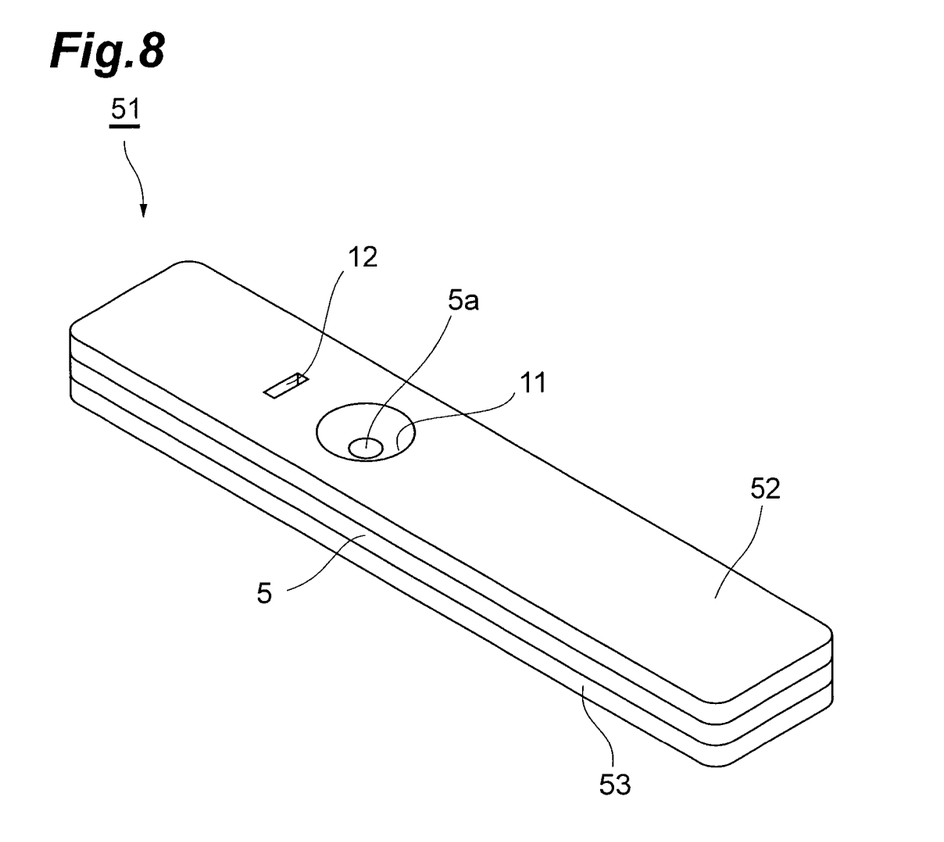
FIG. 8 is a perspective view illustrating the leukocyte measurement device in accordance with yet another modified example of the present invention.
Figure 9:
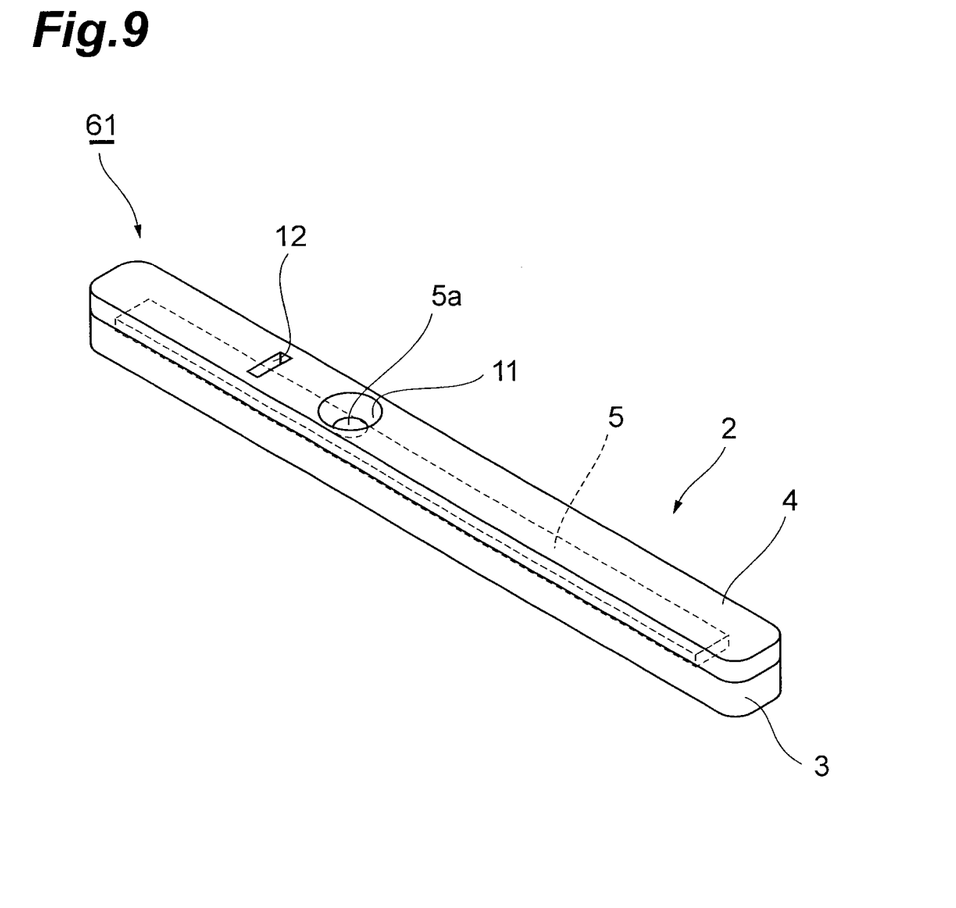
FIG. 9 is a perspective view illustrating the leukocyte measurement device in accordance with a further modified example of the present invention.
Figure 10:
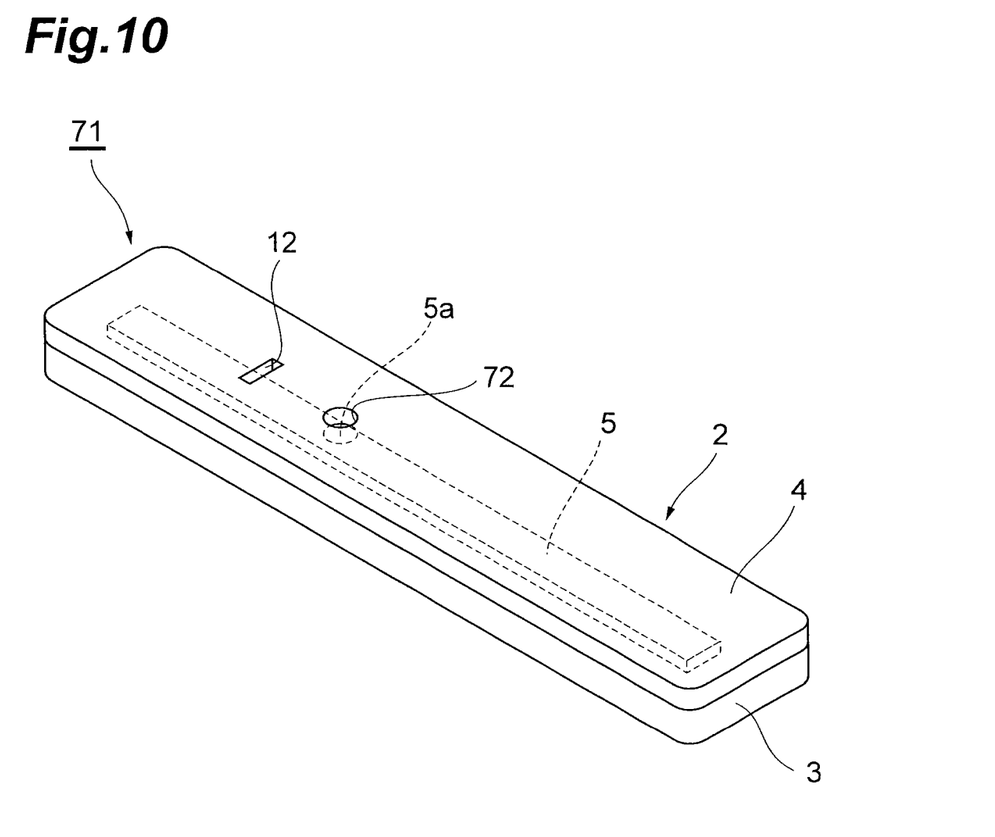
FIG. 10 is a perspective view illustrating the leukocyte measurement device in accordance with a still further modified example of the present invention.

It is not always necessary for the housing 2 to be constituted by the main part 3 and lid part 4; for example, as in a leukocyte measurement device 51 illustrated in FIG. 8, upper and lower plates 52, 53, each shaped into a strip as with the carrier 5, may hold the carrier 5 therebetween. In this case, the upper plate 52 may be provided with the opening part 11 and spread inspection window 12, for example. As in a leukocyte measurement device 61 illustrated in FIG. 9, the housing 2 may have substantially the same width as with the carrier 5, so that the housing 2 is arranged with the carrier 5 without any space therebetween. It is not always necessary for the opening part 11 to be tapered; as in a leukocyte measurement device 71 illustrated in FIG. 10, an opening part 72 having a circular cross section with a fixed diameter may be provided.

EXAMPLES

Examples of the present invention, which do not restrict the present invention, will now be illustrated.

In Example 1, GF/DVA manufactured by GE Healthcare was cut into a width of 4 mm with a length of 110 mm as a carrier and set in a housing having a width of 20 mm and a length of 120 mm, so as to construct a leukocyte measurement device. The housing was provided with an opening part at a longitudinal end part and spread inspection windows (hereinafter referred to as spread inspection windows A to C with increasing distance from the opening part) at respective positions separated by 5 mm, 50 mm, and 100 mm from the opening part. From the opening part, 5 µl of the blood and then 100 µl of normal saline were dropped onto the leukocyte measurement device. As a result, leukocytes were captured at the dropping position, erythrocytes and partly hemolyzed hemoglobin spread longitudinally of the carrier, and red could be seen in the spread inspection window A.

In Example 2, using a leukocyte measurement device similar to that of Example 1, 50 µl of the blood was dropped from the opening part. As a result, leukocytes were captured at the dropping position, erythrocytes spread longitudinally of the carrier, and red could be seen in the spread inspection window A. When 200 µl of distilled water was dropped at the opening part thereafter, red could be seen in the spread inspection window B. When 300 µl of distilled water was further dropped at the opening part, red could be seen in the spread inspection window C.

In Example 3, GF/DVA manufactured by GE Healthcare was cut into a 20-mm square as a carrier and set in a 30-mm square housing, so as to construct a leukocyte measurement device. The housing is provided with an opening part at the center and four spread inspection windows (hereinafter referred to as spread inspection windows A to D) at respective positions separated by 5 mm from the opening part so as to correspond to four corners of the carrier. From the opening part, 50 µl of the blood and then 100 µl of normal saline were dropped onto the leukocyte measurement device. As a result, leukocytes were captured at the dropping position, erythrocytes and partly hemolyzed hemoglobin spread radially from the dropping position, and red could be seen in all of the spread inspection windows A to D.

In Example 4, VFE manufactured by GE Healthcare was cut into a width of 4 mm with a length of 70 mm as a carrier and set in a housing having a width of 16 mm and a length of 80 mm, so as to construct a leukocyte measurement device. The housing is provided with an opening part at the center and one spread inspection window (hereinafter referred to as spread inspection window A) at a position separated by 8 mm from the opening part. From the opening part, 5 µl of the blood and then 50 µl of distilled water were dropped onto the leukocyte measurement device. Further, 50 µl of a POD activity measurement reaction reagent solution (TMB Solution manufactured by Wako Pure Chemical Industries, Ltd.) containing hydrogen peroxide and 3,3',5, 5'-tetramethylbenzidine (TMB) was dropped. As a result, blue coloration by the POD activity of leukocytes could be seen in the opening part. Erythrocytes and partly hemolyzed hemoglobin spread longitudinally of the carrier from the dropping position, and red could be seen in the spread inspection window A.

In Example 5, GF/DVA manufactured by GE Healthcare was cut into a width of 4 mm with a length of 70 mm as a carrier, and 50 µl of an ethanol solution dissolving therein 10 mg of 3-(N-tosyl-L-alanyloxy)indole was dropped as a reaction reagent at a dropping position set at the center of the carrier and then dried for 10 min at 60° C. The carrier was set in a housing similar to that of Example 4, so as to construct a leukocyte measurement device. From the opening part, 5 µl of the blood and then 100 µl of a 0.1 M boric acid buffer having a pH of 8.6 were dropped, so as to start a reaction. As a result, indigo blue coloration by the esterase activity of leukocytes could be seen in the opening part. Erythrocytes and partly hemolyzed hemoglobin spread longitudinally of the carrier from the dropping position, and red could be seen in the spread inspection window A.

In Example 6, a leukocyte measurement device similar to that of Example 1 was constructed. From the opening part, 5 μl of the blood and then 50 μl of a solution diluting an enzyme-labeled antibody (ALP-labeled antineutrophil antibody) with a 10 mM phosphate-buffered solution at a pH of 7.2 containing 150 mM NaCl were dropped onto the leukocyte measurement device. Also, 100 μl of BCIP/NBT Phosphatase Substrate (manufactured by Kirkegaard & Perry Laboratories, Inc.), which was a coloring reagent containing 5-bromo-4-chloro-3-indoxylphosphate (BCIP) and nitroblue tetrazolium (NBT), was dropped from the opening part. As a result, an unreacted part of the enzyme-labeled antibody was washed out, and purple coloration by the ALP activity of the enzyme-labeled antibody combined with leukocytes could be seen in the opening part. Erythrocytes and partly hemolyzed hemoglobin spread longitudinally of the carrier, and red could be seen in the spread inspection window A.

REFERENCE SIGNS LIST 1, 21, 31, 41, 51, 61, 71 . . . leukocyte measurement device; 2, 42 . . . housing; 5, 45 . . . carrier; 5a, 45a . . . dropping position; 11, 72 . . . opening part; 12 . . . spread inspection window; S . . . blood-derived sample

The invention claimed is:

1. A leukocyte measurement device, comprising:
a housing configured with an opening part adapted for dropping a blood-derived sample; and
a carrier, contained in the housing, adapted for capturing leukocytes in components contained in the blood-derived sample dropped from the opening part near a dropping position thereof and for spreading other components containing erythrocytes and/or hemoglobin into a lateral flow direction, wherein said carrier is a fiber filter having a pore size ranging from 3 μm to 10 μm;
wherein the housing is configured with at least one spread inspection window, located at a position separated from the opening part in a spreading direction of the other components, adapted for making at least a part of the carrier visible from outside,
wherein the dropping position of the carrier has a first observed part showing coloring by the leukocytes,
wherein the dropping position of the carrier is impregnated with a part or whole of a reagent adapted for a color reaction by the leukocytes, and
wherein the visible part of the carrier has a second observed part showing a coloring by the erythrocytes and/or hemoglobin, the second observed part containing no control reagent fixed thereto or impregnated therewith.

2. A reagent kit comprising the leukocyte measurement device according to claim 1 and at least one selected from the group consisting of a reagent adapted for a color reaction by the leukocytes, a wash solution, and a diluent.

3. The leukocyte measurement device according to claim 1, wherein whether the leukocyte measurement device has already been used or not is determined by seeing the color of erythrocytes and/or hemoglobin spread through the spread inspection window.

4. The leukocyte measurement device according to claim 1, wherein whether the measurement has been performed appropriately or not is determined by seeing whether there is coloring by erythrocytes and/or hemoglobin or not through the spread inspection window after a predetermined time from the dropping of the blood-derived sample from the opening part.

5. The leukocyte measurement device according to claim 1, wherein the at least one spread inspection window is on the same face of the housing as the opening part.

* * * * *